United States Patent
Moriya et al.

(10) Patent No.: US 9,022,225 B2
(45) Date of Patent: May 5, 2015

(54) FILTRATION FILTER AND PRODUCTION METHOD THEREFOR

(75) Inventors: Tsuyoshi Moriya, Tokyo (JP); Asao Yamashita, Miyagi (JP)

(73) Assignee: Tokyo Electron Limited, Tokyo (JP)

( * ) Notice: Subject to any disclaimer, the term of this patent is extended or adjusted under 35 U.S.C. 154(b) by 55 days.

(21) Appl. No.: 14/006,177

(22) PCT Filed: Mar. 13, 2012

(86) PCT No.: PCT/JP2012/056953
§ 371 (c)(1),
(2), (4) Date: Sep. 19, 2013

(87) PCT Pub. No.: WO2012/128235
PCT Pub. Date: Sep. 27, 2012

(65) Prior Publication Data
US 2014/0008290 A1    Jan. 9, 2014

(30) Foreign Application Priority Data

Mar. 24, 2011  (JP) .................................. 2011-065997
Jul. 15, 2011  (JP) ................................. 2011-156681

(51) Int. Cl.
*B01D 25/00*    (2006.01)
*B01D 29/62*    (2006.01)
(Continued)

(52) U.S. Cl.
CPC ................. *B01D 29/62* (2013.01); *B01D 29/46* (2013.01); *B01D 61/243* (2013.01);
(Continued)

(58) Field of Classification Search
CPC ...... B01D 25/001; B01D 25/08; B01D 25/12; B01D 25/121; B01D 25/122; B01D 25/164; B01D 25/176; B01D 25/18; B01D 25/19; B01D 25/21; B01D 25/215; B01D 25/26; B01D 29/00; B01D 29/0002; B01D 29/0004; B01D 29/0006; B01D 29/012; B01D 29/055; B01D 29/05; B01D 2267/30; B01D 2267/60
USPC ......... 210/232, 255, 321.84, 323.1, 346, 489, 210/490
See application file for complete search history.

(56) References Cited

U.S. PATENT DOCUMENTS

2006/0266692 A1* 11/2006 Foster et al. ............. 210/321.84
2012/0281151 A1* 11/2012 Abe .............................. 348/739

FOREIGN PATENT DOCUMENTS

| JP | 63-107712 A  | 5/1988 |
| JP | 11-200572 A  | 7/1999 |

(Continued)

OTHER PUBLICATIONS

International Search Report mailed Jun. 12, 2012 in PCT/JP2012/056953.

*Primary Examiner* — Allison Fitzsimmons
(74) *Attorney, Agent, or Firm* — Rothwell, Figg, Ernst & Manbeck, P.C.

(57) ABSTRACT

Provided is a filtration filer with which a stable opening size during filtration is obtained, and which can be easily regenerated when clogged and used repeatedly. The filtration filter (10) comprises: a substrate stack wherein substrates (11) that have a through hole that penetrates from front to back are stacked; stoppers (15) that define the spacing between the substrates (11); and pillars (16) with a larger thermal expansion coefficient than the stoppers (15). The spacing between the substrates (11) at normal temperature is defined at least by the stoppers (15), and the spacing when heated is defined by the thermally expanded pillars (16). The gaps between the substrates (11) form the filtration surface that traps contaminants contained in the liquid that is being treated A.

21 Claims, 10 Drawing Sheets

(51) Int. Cl.
   *B01D 29/46*   (2006.01)
   *B01D 63/08*   (2006.01)
   *B01D 39/16*   (2006.01)
   *B01D 39/20*   (2006.01)
   *B01D 61/02*   (2006.01)
   *B01D 61/04*   (2006.01)
   *B01D 69/10*   (2006.01)
   *B01D 29/00*   (2006.01)
   *B01D 61/24*   (2006.01)
   *B01D 65/02*   (2006.01)

(52) U.S. Cl.
   CPC ......... *B01D 63/084* (2013.01); *B01D 2313/14* (2013.01); *B01D 39/16* (2013.01); *B01D 39/1692* (2013.01); *B01D 39/2003* (2013.01); *B01D 39/2027* (2013.01); *B01D 39/2055* (2013.01); *B01D 39/2068* (2013.01); *B01D 61/025* (2013.01); *B01D 61/04* (2013.01); *B01D 65/02* (2013.01); *B01D 69/10* (2013.01); *B01D 2311/04* (2013.01); *B01D 2311/06* (2013.01); *B01D 2313/02* (2013.01); *B01D 2321/04* (2013.01); *A61M 2205/7563* (2013.01)

(56) References Cited

FOREIGN PATENT DOCUMENTS

| | | |
|---|---|---|
| JP | 2002-186810 A | 7/2002 |
| JP | 2003-210916 A | 7/2003 |
| JP | 2007-130532 A | 5/2007 |
| JP | 2010-247107 A | 11/2010 |

* cited by examiner

FILTRATION FILTER AND PRODUCTION METHOD THEREFOR

CROSS REFERENCE TO RELATED APPLICATIONS

This application is a 35 U.S.C. 371 National Phase Entry Application from PCT/JP2012/056953, filed Mar. 13, 2012, which claims the benefit of Japanese Patent Application Nos. 2011-065997, filed Mar. 24, 2011 and 2011-156681, filed Jul. 15, 2011, the disclosures of which are incorporated herein in their entirety by reference.

TECHNICAL FIELD

The present disclosure relates to a filtration filter and a method of producing the same.

BACKGROUND

Filtration filters are frequently used when purifying service water by removing contaminants or impurities from, for example, waste water of a sewage treatment plant which treats sewage such as factory waste water or living drainage, or when purifying fresh water by removing, for example, salt from seawater. Such filtration filters are known to be made up of a polymer material such as, for example, reverse osmosis membranes using a polymer membrane of methyl acetate. The reverse osmosis membranes have countless through holes with a diameter of several nanometers. When sewage or seawater is pressed and passed through the reverse osmosis membranes, water molecules pass the through holes in which the diameter of one water molecule is about 0.38 nm. However, molecules of contaminants having a size of dozens of nanometers or sodium ions around which water molecules are coordinated due to hydration cannot pass the through holes. As a result, the reverse osmosis membranes purify service water or fresh water from the sewage or seawater by separating the water molecules from the contaminants or sodium ions.

However, when service water is purified from waste water using such reverse osmosis membranes in a developing country or a distressed area with a natural disaster, bacteria in the waste water decompose the polymer membranes. Thus, there is a problem in that the lifespan of the reverse osmosis membranes are extremely shortened.

In addition, since the reverse osmosis membranes use a polymer membrane as a principal constituent element, the reverse osmosis membranes are poor in strength. Thus, there is a problem in that, when the pressure applied to sewage or seawater (primary side pressure) is increased in order to enhance the purification efficiency, the reverse osmosis membranes may be torn.

Thus, filtration filters in which a zeolite membrane for separation which is stable without being decomposed by bacteria is used have been recently used. See, for example, Patent Document 1 and Patent Document 2.

PRIOR ART DOCUMENT

Patent Document

Patent Document 1: Japanese Patent Lai-Open Publication No. Hei 11-200572
Patent Document 2: Japanese Patent Laid-Open Publication No. 2010-247107

DISCLOSURE OF THE INVENTION

Problems to be Solved

In the above-described filtration filter using zeolite, it is certain that the zeolit has openings of dozens of nanometers. However, there is a problem in that, since gaps exceeding the openings exist between zeolite cells, a constant opening diameter may not be obtained and thus, a high filtration precision may not be obtained.

An object of the present disclosure is to provide a filtration filter which allows a stable opening to be obtained during filtration and a method of producing the same.

Means to Solve the Problems

In order to solve the above-described problems, according to a first aspect of the present disclosure, provided is a filtration filter that includes: a substrate stack formed by stacking a plurality of substrates each having a through hole that penetrates the substrate from front to back; one or more first spacing maintaining members that define a spacing between adjacent substrates in the substrate stack; and one or more second spacing maintaining members having a thermal expansion coefficient that is larger than that of the one or more first spacing maintaining members. The spacing between adjacent substrates at normal temperature is defined at least by the one or more first spacing maintaining members, the spacing when heated is defined by the one or more second spacing maintaining members in a thermally expanded state, and gaps between adjacent substrates form a filtration surface that traps target components contained in a liquid to be treated.

Effect of the Invention

According to the present disclosure, at normal temperature, the spacing between the substrates may be stably defined at least by the first spacing maintaining member and, during regeneration, the second spacing maintaining members may be thermally expanded to widen the spacing between the substrates. As a result, a stable opening may be obtained during a filtration treatment.

DETAILED DESCRIPTION TO EXECUTE THE INVENTION

Figure 1:
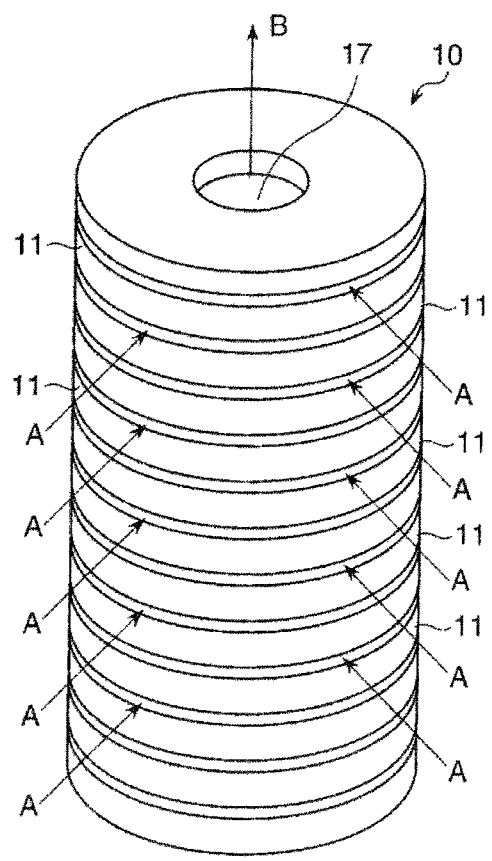
FIG. 1 is a perspective view illustrating a filtration filter according to the present disclosure.

In order to solve the above-described problems, according to a first aspect of the present disclosure, provided is a filtration filter that includes: a substrate stack formed by stacking a plurality of substrates each having a through hole that penetrates the substrate from front to back; one or more first spacing maintaining members that define a spacing between adjacent substrates in the substrate stack; and one or more second spacing maintaining members having a thermal expansion coefficient that is larger than that of the one or more first spacing maintaining members. The spacing between adjacent substrates at normal temperature is defined at least by the one or more first spacing maintaining members, the spacing when heated is defined by the one or more second spacing maintaining members in a thermally expanded state, and gaps between adjacent substrates form a filtration surface that traps target components contained in a liquid to be treated.

In the first aspect of the present disclosure, it is preferable that the substrates have a thick wall portion and a thin wall portion, a plurality of first spacing maintaining members are disposed between the thick wall portions to be spaced apart from each other, a plurality of second spacing maintaining members are disposed between the thin wall portions to be spaced apart from each other, and the length of the one or more second spacing maintaining members is longer than the length of the one or more first spacing maintaining members.

In the first aspect of the present of the present disclosure, it is preferable that the thick wall portion forms a perimeter portion of the substrate, the thin wall portion forms a central portion of the substrate which is surrounded by the thick wall portion, and the through hole is provided at the central portion of the thin wall portion.

In the first aspect of the present disclosure, it is preferable that the thick wall portion is arranged in an annular shape on the front surface of the substrate so that the entire length of the thick wall portion is longer than the perimeter portion of the substrate, the thin wall portion is surrounded by the thick wall portion and also includes the central portion of the substrate, and the through hole is provided at the central portion of the substrate.

In the first aspect of the present disclosure, it is preferable that the thick wall portion is arranged on the front surface of the substrate in a loop shape in which two rows of zigzag-shaped line portions are connected to each other at the ends thereof, respectively.

In the first aspect of the present disclosure, it is preferable that the through hole is communicated with through holes of other substrates in the substrate stack, thereby forming a flow path for a liquid to be treated or filtrate.

In the first aspect of the present disclosure, it is preferable that the thick wall portion of the substrate has a surface roughness (Ra) which is not more than ⅒ of a gap between the thick wall portions.

In the first aspect of the present disclosure, it is preferable that each of the substrates is made up of at least one of silicon, glass, a metal, a silicon compound including silicon carbonate, a resign including polyimide, and carbon.

In the first aspect of the present disclosure, the substrate stack is integrated by a fastening member which allows the thermal expansion of the second spacing maintaining members.

In order to solve the above-described problems, according to a second aspect of the present disclosure, provided is a method of producing a filtration filter which includes: a spot facing step of forming a spot face portion at a central portion of a substrate, thereby forming a thick wall portion that forms a perimeter portion of the substrate and a thin wall portion surrounded by the thick wall portion; a through hole forming step of forming a through hole that penetrates the substrate from front to back at a central portion of the thin wall portion; a first spacing maintaining member forming step of forming a plurality of first spacing maintaining members with a predetermined height at a predetermined interval on the thick wall portion; a second spacing maintaining member forming step of forming a plurality of second spacing maintaining members on the thin wall portion at a predetermined interval, the second spacing maintaining members having a thermal expansion coefficient larger than that of the first interval maintaining members and being longer than the first spacing maintaining members; and a stacking step of stacking a plurality of substrates via at least the first interval maintaining members.

In the second aspect of the present disclosure, it is preferable that, in the spot facing step, the spot face portion is formed through a plasma etching using plasma.

In the second aspect of the present disclosure, it is preferable that, in the spot facing step, the spot face portion is formed through a chemical mechanical polishing (CMP) method.

In the second aspect of the present disclosure, it is preferable that, in the spot facing step, the spot face portion is formed through a chemical mechanical polishing (CMP) method.

In the second aspect of the present disclosure, it is preferable that, in the first spacing maintaining member forming step, the first spacing maintaining members made up of a photoresist are formed on the thick wall portion through a coating method using a mask material.

In the second aspect of the present disclosure, it is preferable that the method further includes an integrating step of integrating the substrate stack stacked in the stacking step by a fastening member which allows thermal expansion of the second spacing maintaining members.

In the second aspect of the present disclosure, it is preferable that the thick wall portions of the substrates have a surface roughness which is not more than gaps between the thick wall portions.

In the second aspect of the present disclosure, it is preferable that at least one of a silicon plate, a glass plate, a metal plate, a plate of a silicon compound including silicon carbonate, a plate of a resin including polyimide, and a carbon plate is used as the substrates.

In order to solve the above-described problems, according to a third aspect of the present disclosure, provided is a method of producing a filtration filter which includes: a masking step of forming an annular masking material along a perimeter portion of a front surface of a substrate; a first etching step of etching the substrate formed with the annular masking material so that a thin wall portion surrounded by a convex portion which corresponds to the annular masking material is formed; a first masking material peeling step of peeling a part of the masking material on the convex portion after the first etching step is terminated; a second etching step of etching the substrate after the first masking material peeling step so that a thick wall portion is formed by the convex portion other than a portion coated with the masking material remaining after the first masking material peeling step and a spacing maintaining portion protruding from the thick wall portion is formed by the convex portion of the portion coated with the remaining masking material; a through hole forming step of forming a through hole that penetrates the substrate from front to back at a central portion of the thin wall portion surrounded by the thick wall portion; a spacing maintaining member forming step of forming a plurality of spacing maintaining members on the thin wall portion of the substrate formed with the through hole at a predetermined spacing, the plurality of spacing maintaining members having a thermal expansion coefficient larger than that of the spacing maintaining portion and having a height higher than that of the spacing maintaining portion; a second masking material peeling step of peeling the masking material from the spacing maintaining portion; and a stacking step of stacking a plurality of substrates at least via the spacing maintaining portion.

In the third aspect of the present disclosure, it is preferable that the method further include an integration step of integrating the substrate stack stacked in the stacking step by a fastening member that allows thermal expansion of the spacing maintaining member.

In the third aspect of the present disclosure, it is preferable that the surface roughness (Ra) of the thick wall portions of the substrates is not more than $1/10$ of the gaps between the thick wall portions.

In the third aspect of the present disclosure, it is preferable that any one of a silicon plate, a glass plate, a ceramic plate, a metal plate, a plate of a silicon compound including silicon carbonate, a plate of a resin including polyimide, and a carbon plate is used as the substrates.

Hereinafter, exemplary embodiments of the present disclosure will be described with reference drawings.

FIG. 1 is a perspective view illustrating a filtration filter according to a first exemplary embodiment of the present disclosure.

Referring to FIG. 1, the filtration filter 10 is configured as a cylindrical substrate stack in which a plurality of disc-shaped substrates 11 are staked at a predetermined spacing and the spacing between the substrates 11 defines an opening width in a filtration surface.

A liquid to be treated A flows into the filtration filter 10 through gaps formed between the substrates 11 on the outer circumferential surface of the cylindrical filtration filter 10, flows toward the central axis, flows through a flow path 17 formed along the central axis as, for example, up-flow, and is recovered as filtrate. In this case, the outer circumferential surface of the filtration filter 10 serves as a filtration surface and contaminants which are target components of filtration are trapped in the gaps on the outer circumferential surface between the substrates 11.

Next, a method of producing the filtration filter according to the first exemplary embodiment will be described.

FIGS. 2A to 2F are process views illustrating a method of producing the filtration filter according to the first exemplary embodiment.

Referring to FIGS. 2A to 2F, the filtration filter 10 is produced in the following manner.

Figure 2A:
FIG. 2A is a process view illustrating a method of producing the filtration filter according to the present disclosure.

First, substrates 11 as a constituent material are prepared (FIG. 2A). The substrates 11 are silicon substrates which have a smooth surface. Circular substrates have a disc shape with a diameter of about 5 mm to 450 mm, and rectangular substrates have a rectangular plate shape of which one side is about 5 mm to 450 mm. The thickness of the substrates 11 is, for example, 0.8 mm to 1.2 mm. The surface roughness (Ra) of the silicon substrates is not more than $1/10$ of the gaps between the thick wall portions of the substrates 11, for example, about 0.1 mm. The thick wall portions will be described later. Besides the silicon substrates, glass substrates, ceramic substrates and metal substrates may be suitably used. In addition, the substrates 11 may be a rectangular plate or a hexagonal plate rather than a disc. In such a case, the filtration filter 10 will be a prismatic pillar or a hexagonal pillar.

Figure 2B:
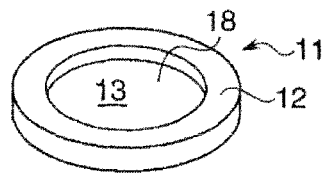
FIG. 2B is a process view illustrating a method of producing the filtration filter according to the present disclosure.

Next, a spot face portion 18 is formed at the central portion of the front surface of each substrate 11 (FIG. 2B). When forming the spot face portion, a semiconductor manufacturing technology may be properly used. That is, the substrate 11 is spot-faced by performing a plasma etching processing in which the substrate 11 is accommodated and supported within, for example, a processing chamber of a plasma etching apparatus, exposed to plasma in a state where the portion other than the spot face portion of the substrate 11 is covered by a mask material and subjected to an etching processing. As a result, the spot face portion 18 is formed on the front surface of the substrate 11 in which, for example, the spot face portion 18 has a dam width of 0.1 mm to 10 mm at the perimeter portion thereof and a depth of 0.1 mm to 0.6 mm. By this, the substrate 11 is formed with a thick wall portion 12 configured by the dam of the perimeter portion and a thin wall portion 13 surrounded by the thick wall portion 12 (see, e.g., FIG. 3 to be described later).

Figure 2C:
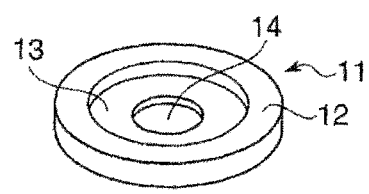
FIG. 2C is a process view illustrating a method of producing the filtration filter according to the present disclosure.

Subsequently, a through hole 14 is formed at the central portion of the thin wall portion 13 which forms the bottom of the spot face portion 18 to penetrate the substrate 11 from front to back (FIG. 2C). Like the spot face portion 13, a plasma etching technology may also be suitably used for forming the through hole 14. The through hole 14 is communicated with through holes of other substrates, thereby forming a flow path 17 for a liquid to be treated or a filtrate in the filtration filter 10. The diameter of the through hole 14 is, for example, 1 mm to 100 mm.

Figure 2D:
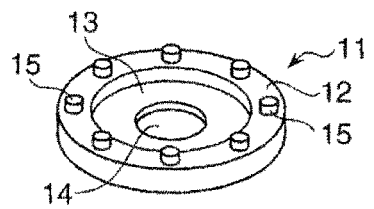
FIG. 2D is a process view illustrating a method of producing the filtration filter according to the present disclosure.

Next, stoppers as first spacing maintaining members that define the spacing between the substrates 11 are formed on the thick wall portion 12 (FIG. 2D). First, a mask material, which is made up of polyimide and formed with openings of which the number and diameter correspond to those of cylindrical stoppers 15, is disposed on the thick wall portion 12 of the substrate 11 and, for example, platinum (Pt) is deposited through a chemical vapor deposition (CVD) method so that cylindrical stoppers 15 with a diameter of 0.1 mm to 10 mm and a height of 10 mm to 20 mm are formed at an interval of, for example, 1 mm to 100 mm. The height of the stoppers 15 may be adjusted by controlling the deposition time. The height may be monitored by providing a sensor that detects the thickness, or the height may be adjusted through an etch back process after deposition to a proper thickness. In FIG. 2D, eight stoppers 15 are formed at an equidistant interval on the thick wall portion 12 that forms the perimeter portion of the substrate 11. Besides platinum, for example, a resin such as polyimide, ceramics, glass, silicon, and SiC, may be suitably used as a material for the stoppers 15. In addition, besides the chemical vapor deposition (CVD) method, all the film forming methods such as, for example, a physical vapor deposition (PVD) method, an atomic layer deposition (ALD) method, and a molecular layer deposition (MLD) method may be used as a method for forming the stoppers 15. The shape, number and interval of the stoppers are not particularly limited. In the present exemplary embodiment, a case in which the stoppers 15 have a cylindrical shape has been described. However, the stoppers 15 may have any shape such as a prismatic shape. The shape, number and interval of the stoppers may be changed by exchanging the mask material.

Figure 2E:
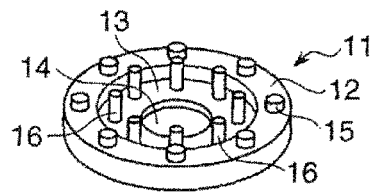
FIG. 2E is a process view illustrating a method of producing the filtration filter according to the present disclosure.

Next, a plurality of the substrates 11 formed with the stoppers 15 are stacked via second spacing maintaining members. First, pillars 16 as the second maintaining members are arranged along the circumferential direction of the thin wall portion 13 of the substrate 11 at an equidistant interval of, for example, 1 mm to 100 mm (FIG. 2E). The pillars 16 are formed through a known method.

The number and interval of the pillars 16 are not particularly limited and may be acceptable if they allow the spacing between adjacent substrates 11 to be correctly defined. The pillars 16 are cylindrical bodies made up of a material of which the thermal expansion coefficient is larger than that of the material of the stoppers 15, for example, aluminum, and, when the pillars 16 are arranged on the thin wall portion 13, the top end surfaces of the pillars 16 are adjusted to have a height where the top end surfaces form a coplanar plane with the top end surfaces of the stoppers 15. That is, the height of the pillar 16 equals to the sum of the depth of the spot face portion 18 and the height of the stoppers 15. Besides the aluminum, for example, gold (Au), zinc, silver, chrome, tin, iron, copper, lead, nickel, aluminum, bronze, brass, duralumin, stainless steel may be suitably used as the material of the pillars 16. In addition, besides the metals, for example, a photoresist, polyester, polyethylene, polyvinyl chloride, polystyrene, and polycarbonate may also be used. Since these materials have a relatively large heat expansion coefficient and thus, the expansion length when heated is long, the gaps between the substrates 11 when heated may be widened. Even in a case where the same material as the stoppers 15 is used as the material for the pillars 16, the gaps between the substrates 11 may be widened due to the difference between the expansion lengths thereof. Thus, when there is any restriction in the materials of the pillars 16 and the stoppers 15, the same material may be used for the pillars 16 and stoppers 15.

Figure 2F:
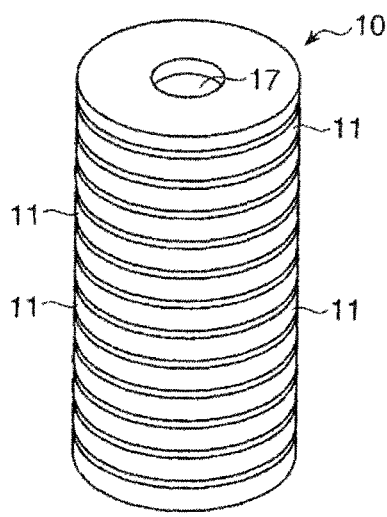
FIG. 2F is a process view illustrating a method of producing the filtration filter according to the present disclosure.

Next, the substrates 11 on which the pillars 16 are arranged are sequentially stacked to form a filtration filter 10 as a substrate stack (FIG. 2F). In this case, an adhesive may be applied to required portions such as the stoppers 15 as needed. An elastic adhesive, in particular, a flexible adhesive, is desirable so as to allow the thermal expansion of the pillars 16 so as to widen the gaps between the substrates 11 when heated.

In the present exemplary embodiment, for example, methods of providing the spot face portion 18, forming the stoppers 15, and forming the through hole 14 are not particularly limited, any method of forming a predetermined spot face portion 18 on a substrate with a required surface roughness or any method of forming stoppers 15 of a predetermined at predetermined positions may be used. Besides the plasma etching, CMP (Chemical Mechanical Polishing) may also be used in forming the spot face portion 18 or the through hole 14 and a CVD method, an ALD method, a sputtering, a plasma etching or a combination thereof may be applied in forming the stoppers 15.

Next, the filtration filter according to the first exemplary embodiment produced through the method illustrated in FIGS. 2A to 2F will be described.

Figure 3:
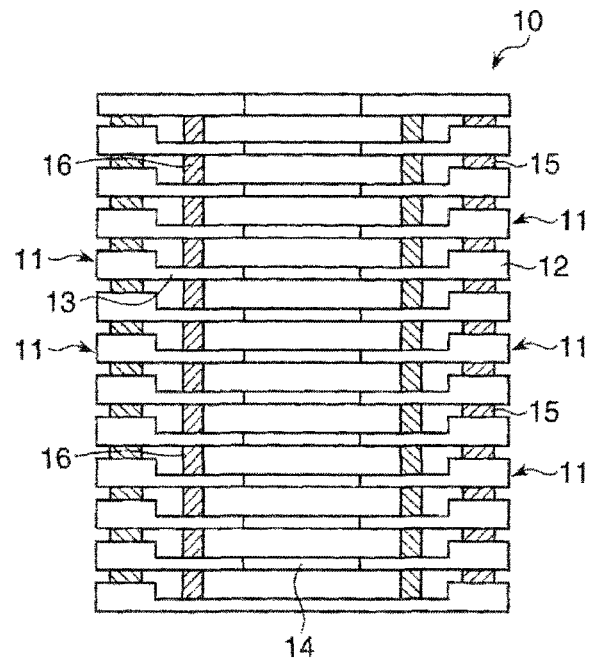
FIG. 3 is a vertical cross-sectional view of the filtration filter.
Figure 4:
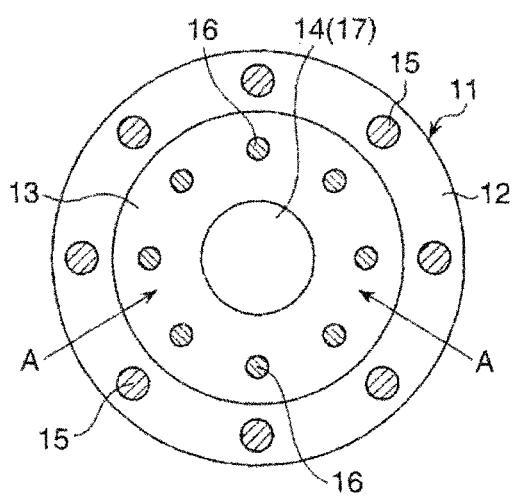
FIG. 4 is a plan view of a substrate which is a constituent element of the filtration filter.

FIG. 3 is a vertical cross-sectional view of the filtration filter according to the first exemplary embodiment and FIG. 4 is a plan view of a substrate which is a constituent element of the filtration filter.

Referring to FIG. 3, a plurality of substrates 11 are stacked via thick wall portions 12, a plurality of stoppers 14 provided on the thick wall portions 12, and a plurality of pillars 16 arranged around the thin wall portions 13 formed with a through hole 14 at the central portion thereof, thereby forming a filtration filter 10.

As for the lowermost substrate 11 which forms the bottom portion of the filtration filter 10, a substrate which does not have the through hole 14 is applied, and as for the uppermost substrate 11 which forms the cover portion of the filtration filter 10, a substrate 11 which does not have the spot face portion 18 is applied.

Referring to FIG. 4, the substrate 11 includes a thick wall portion 12 that forms the perimeter portion thereof and a thin wall portion 13 surrounded by the thick wall portion 12, and a plurality of stoppers 15 are provided on the top of the thick wall portion 12. The height of the stoppers 15 defines the spacing between the substrates 11 and defines an opening width at normal temperature, that is, during filtering in a normal temperature processing. As an aspect, the outer circumferential surface of the filtration filter 10 serves as the filtration surface and contaminants such as, for example, various germs are trapped by the gaps between the substrates 11 on the outer circumferential surface, and a space enclosed by adjacent substrates 11 and adjacent stoppers 15 forms a flow path for a liquid to be treated.

Next, the function of the filtration filter 10 will be described.

In the filtration filter 10, the stoppers 15 are made up of a material which is relatively stable to a thermal change and has a small thermal expansion coefficient, and the pillars 16 are made up of a material which is relatively sensible to a thermal change and has a large thermal expansion coefficient. The thermal expansion coefficient of platinum which is suitably used as the material of the stoppers 15 is $9(\times 10^{-6}/°C.)$, and the thermal expansion coefficient of the metal aluminum which is suitably used as the material of the pillars 16 is 23(×10⁻⁶/° C.). Since the top end surfaces of the stoppers of the stoppers 15 and the top end surfaces of the pillars 16 are in a coplanar plane at normal temperature, the spacing between the substrates 11 at normal temperature is stably defined by the stoppers 15 and the pillars 16. Herein, the normal temperature is 25° C.±15° C. and is 25° C. unless described otherwise.

The filtering processing using the filtration filter 10 is typically performed at normal temperature.

As illustrated in FIG. 1, the liquid to be treated A that contains contaminants such as various germs flows into the cylindrical filtration filter 10 from the gaps between the substrates 11 in the outer circumferential surface of the cylindrical filtration filter 10, flows toward the central axis, flows as, for example, up-flow, through the flow path 17 formed by through holes 14 which are communicated with each other, and flows out from the filtration filter 10. When the height of the stoppers 15, i.e., the opening width is set to 10 nm, for example, the various germs contained in the liquid to be treated A and having an outer diameter larger than 10 nm are trapped by the gaps between the substrates 11.

When the filtration treatment at normal temperature is continued over a predetermined length of time and solid materials such as various germs are deposited in the gaps between the substrates 11 on the outer circumferential surface of the cylindrical body which is the filtration surface, thereby delaying the filtration rate, the filtration filter 10 is regenerated. The regeneration of the filtration filter 10 is performed as follows.

First, supply of the liquid to be treated A is stopped, and a backwash water of, for example, 75° C. flows into the flow path 17 formed along the central axis of the substrate stack in a direction in reverse to that in the filtration treatment. As the backwash water, a part of the liquid recovered as the filtrate is used, for example.

When the backwash water of 75° C. is caused to flow through the filtration filter 10, the stoppers 15 disposed between the thick wall portions 12 of the substrates 11 are not expanded so much since the thermal expansion coefficient of the stoppers 15 is small. However, the pillars 16 disposed between the thin wall portions 13 are expanded since the pillars 16 have a large thermal expansion coefficient. In addition, since the pillars 16 are longer than the stoppers 15, the expansion length is long. As a result, the spacing between the thin wall portions 13 of the substrates 11 and the spacing between the thick wall portions 12 are widened. For example, the spacing between the thick wall portions 12 may be widened from 10 nm to 700 nm.

When the spacing between the thick wall portions 12 of the substrates 11 is widened, the trapping of the contaminants such as various germs which have been trapped by the gaps between the substrates 11 are released and the contaminants are discharged from the filtration filter 10 along the flow of the backwash flow. As a result, the filtration filter 10 is regenerated.

Assuming that the thickness of the thick wall portions 12 of the substrates 11 is 1 mm, the thickness of the thin wall portions 13 is 0.4 mm, the height of the stoppers made up of platinum at normal temperature, i.e., the gap between the thick wall portions 12 is 10 nm, the height of the pillars 16 made up of metal aluminum at normal temperature is 0.6 mm (accurately, 0.6 mm±10 nm), and the temperature of the backwash water is 75° C., the expansion length of the pillars 16 on the substrates 11 will be as follows.

Since the thermal expansion coefficient of the metal aluminum is 23(×10⁻⁶/° C.), the expansion length of the pillars 16 is as follows.

600 (μm)×23(×10⁻⁶)×(75−25)×1000=690 (nm).

That is, when backwashing is performed with backwash water of 75° C., the height of the pillars 16 is increased 690 nm, and as a result, the spacing between the thick wall portions 12 between adjacent substrates 11 is increased, thereby being greatly widened as compared to 10 nm at normal temperature. Thus, the contaminants such as various germs which have been trapped in the gaps between the thick wall portions 12 of the substrates 11 are easily released.

Figure 5:
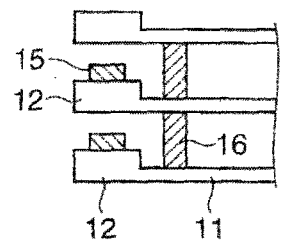
FIG. 5 is an enlarged view illustrating a portion where the spacing between the thick wall portions of the substrates is increased.

FIG. 5 is a partial enlarged view of the filtration filter 10 in which the spacing between the thick wall portions 12 of the substrates 11 are widened. Referring to FIG. 5, the pillars 16 are thermally expanded and thus, the spacing between the thick wall portions 12 of the substrates 11 is widened. Accordingly, the regeneration by backwashing becomes easy.

When the water of normal temperature from which the contaminants such as various have been removed, for example, the liquid recovered as a filtrate, is allowed to flow through the filtration filter 10, the pillars 16 are cooled to normal temperature, and thus, the acting force of widening the spacing between the substrates 11 disappears so that the spacing between the thick wall portions 12 of the substrates 11 returns to 10 nm during the filtration treatment.

In the filtration filter according to the present exemplary embodiment, since the gaps may be widened by heating, the cleaning may also be performed by allowing the cleaning water to flow in the forward direction rather than in the reverse direction. In this case, the various germs trapped in the gaps are released from the widened gaps and caused to flow by the cleaning water so that the cleaning may be performed. However, since the contaminants are caused to pass through the inside of the filter, it is desirable to cause the cleaning water to flow in the reverse direction as described above, if possible. However, when it is difficult to cause the cleaning water to flow in the reverse direction due to a situation of a system, the cleaning water may be allowed to flow in the forward.

According to the present exemplary embodiment, when performing the filtration treatment at normal temperature, the gap between the thick wall portions 12 of the substrates 11 may be mainly defined by the stoppers 15, for example, to 10 nm, and during the regeneration, the spacing between the thick wall portions 12 of the substrates 11 may be widened to about 700 nm by the pillars 16 using heated water. Thus, during filtration treatment, a stable opening may be obtained and, during regeneration, trapped materials are released by widening the openings so that the regeneration may be easily performed.

In addition, according to the present exemplary embodiment, since the outer circumferential surface of the cylindrical body serves as the filtration surface so that the filtration area may be taken widely, the processing performance may be enhanced.

Further, according to the present exemplary embodiment, a semiconductor manufacturing technology may be applicable as, for example, a processing method of the substrates 11, a precise filtration filter may be produced using a constituent material with a high size precision.

In the present exemplary embodiment, it has been described that the length of the pillars 16 equals to the sum of the depth of the spot face portion 18 and the height of the stoppers 15 and the spacing between the substrates 11 at normal temperature is defined by the stoppers 15 and the pillars 16. However, the length of the pillars 16 may also be set to be somewhat shorter than the sum of the depth of the spot face portion 18 and the height of the stoppers 15 so that the spacing between the substrates 11 at normal temperature is defined only by the stoppers 15 and the spacing between the substrates 11 when heated is defined by the thermally expanded pillars 16.

In the present exemplary embodiment, the number of stacked substrates 11 is not particularly limited and may be adjusted according to a requested filtration treatment capability. For example, several or dozens of cylindrical filters formed by stacking 100 substrates per each filter may be connected in series. By this, a filtration filter with a high processing capability may be implemented.

Next, the action of the filtration filter according to the present disclosure will be described. Although the use of the filtration filter of the present disclosure is not particularly limited, it may be suitably applied as a tap water purification filter in a water purification plant.

Figure 6:
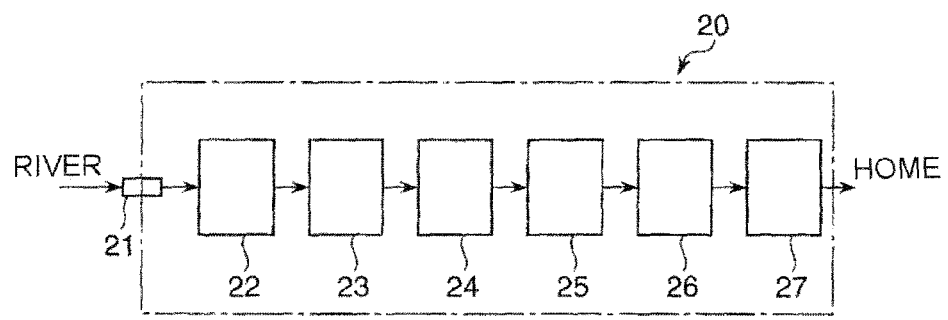
FIG. 6 is a block diagram illustrating a configuration of a water purification plant to which the filtration filter according to the present disclosure may be applied.

FIG. 6 is a block diagram illustrating a configuration of a water purification plant where the filtration filter according to the present disclosure may be applied.

Referring to FIG. 6, the water purification plant 20 includes, for example, a water intake 21 that takes in river water, for example, from a river and a flocculent settling basin 22 that removes solid materials contained in the taken river water, and further includes a rapid filter basin 23, an ozone contact basin 24, an activated carbon adsorption basin 25, a chlorine mixing basin 26, and stilling basin 27 which are provided in this order in the wake flow of the flocculent settling basin 22.

The river water taken by the water intake 21 flows into a depositing basin (not illustrated) called a sand basin where solid materials such as sands are subjected to a settling separation, and then the river water is sent to the flocculent settling basin 22. To the water flown into flocculent settling basin 22, for example, a flocculent is added so that solid materials such as plankton are flocculated, precipitated and separated, and only the supernatant water is sent to the rapid filter basin 23 of the wake flow. The water flown into the rapid filter basin 23 passes through a filtration layer in which, for example, fine sands are filled so that finer solid materials may be removed, and then the water is sent to the ozone contact basin 24 of the wake flow.

The water flown into the ozone contact basin 24 comes into contact with ozone in the ozone contact basin 24 so that substances causing haze or odor are decomposed, and then, is flown into the activated carbon adsorption basin 25 of the wake flow. The water flown into the activated carbon adsorption basin 25 is subjected to an adsorption treatment of fine substances which have not been fully removed by the ozone and then, the water is flown into the chlorine mixing basin 26 where a predetermined amount of chlorine is blended into the water to sterilize the water. The water sterilized with the chlorine is stored in the stilling basin 27 as tap water for beverage and supplied to, for example, general homes, as needed.

In the water purification plant 20, the filtration filter 10 is applied as an alternative equipment of the ozone contact basin 24 and the activated carbon adsorption basin 25, for example.

That is, the water discharged from the rapid filter basin 23 flows into the filtration filter 10 as a liquid to be treated A so as to separate contaminants unremoved by the rapid filter basin 23, such as for example, various germs of not less than 10 nm, thereby being purified.

The liquid to be treated A of real temperature, for example, 25° C., flows into the filtration filter 10 from the gaps between the substrates 11 of the filtration surface formed on the outer circumferential surface of filtration filter, flows toward the central axis, and passes through the flow path 17 formed along the central axis, thereby being recovered as a treated liquid B (see FIG. 1), and is flown into the chlorine mixing basin 26 of the wake flow. The filtrate of the filtration filter 10 flown into the chlorine mixing basin 26 is subjected to the sterilization treatment by adding a predetermined amount of chlorine thereto, and then stored in the stilling basin 27. Meanwhile, the contaminants such as various germs are trapped and separated on the filtration surface which is the outer circumferential surface of the filtration filter 10.

The spacing between the thick wall portions 12 of the substrates 11 which is defined by the stoppers 15 is, for example, 10 nm, and the contaminants larger than the spacing such as, for example, influenza virus, are certainly captured on the filtration surface.

When the filtration surface is clogged and the filtration rate is reduced after having continued the filtration treatment of, for example, various germs, the regeneration of the filtration filter 10 is performed. That is, in the clogged filtration filter 10, the supply of the outlet liquid of the rapid filter basin 23 as the liquid to be treated A is stopped, and backwash water is caused to flow in the reverse direction to the flowing direction of the liquid to be treated A, for example. As the backwash water, for example, the inlet water to the chlorine mixing basin 26 which is the filtrate of the filtration filter 10 is used. During this, the temperature of the backwash temperature is heated to a temperature of, for example, 70° C. to 80° C., which is higher than normal temperature.

As described above, after the backwash water has flown through the filtration filter 10, the gaps between the thick wall portions 12 of the substrates 11 that form the filtration surface are widened and the trap of the contaminants such as various germs trapped in the gaps is released and thus, the filtration filter 10 is regenerated. The backwash water containing, for example, the various germs released from the filtration surface may be returned to, for example, the previous flow of the flocculent settling basin 22 or separately treated.

According to the present exemplary embodiment, the openings in the filtration surface of the filtration filter 10 may be greatly changed at normal temperature when the filtration treatment is performed and when heated to perform the regeneration. As a result, during the filtration treatment, contaminants such as various germs may be stably separated with a predetermined opening diameter and, during the regeneration, the trapped contaminants may be easily released so that the regeneration may be easily performed.

In the present exemplary embodiment, since the filtration filter 10 is configured by a substrate stack, the mechanical strength is high so that pressure filtration may be performed. Thus, the processing time may be shortened by increasing the processing amount of liquid.

In the present exemplary embodiment, it is preferable that plural systems of filtration treatment lines of the filtration filters 10 are provided. By this, when one system is clogged and regenerated, the filtration treatment may be continued by other systems.

In the present exemplary embodiment, the filtration filter 10 has been applied as a water purification apparatus in a water purification plant. However, the filtration filter 10 may also be applied for medical purpose as, for example, a component separation apparatus for blood or protein or a filtration apparatus for artificial dialysis. In addition, it may also be applied as a purification apparatus of cleaning water for use in a wet cleaning in a semiconductor manufacturing factory.

In the present exemplary embodiment, as for the constituent material of the pillars 16, a material which has a converse piezoelectric effect such as, for example, quartz ($SiO_2$), zinc oxide (ZnO), Rochelle salt (potassium sodium tartarte) ($KNaC_4H_4O_6$), (lead zirconate titante (PZT:$Pb(Zr,Ti)O_3$), lithium niobate (LiNbO$_3$), lithium tantalate (LiTaO$_3$), lithium tetraborate (Li$_2$B$_4$O$_7$), langasite (La$_3$Ga$_5$SiO$_{14}$), aluminum nitride (AlN), gemstone (tourmaline), polyvinylidene fluoride (PVDF), gallium phosphate (GaPO$_4$), or gallium arsenide (GaAs), may be used, instead a material of which the thermal expansion coefficient is higher than that of the constituent material of the stoppers 15. These materials are suitable as a pillar material since they may be expanded when a voltage is applied thereto. The thermal expansion length obtained by applying a voltage to these materials is substantially identical to the thermal expansion length in a material of which the thermal expansion coefficient is large.

When the life of the filtration filter 10 according to the present exemplary embodiment as a filtration apparatus comes to end, substantially 100% of the base material of the filtration filter 100 may be reused by disassembling the filtration filter 10 and removing the stoppers 15 or the like that are attached to the substrates 11.

In the present exemplary embodiment, the stoppers 15 and the substrates 11 directly positioned thereon may be integrated by applying an adhesive to the contact surfaces of the substrates 11. Meanwhile, the entire filtration filter 10 as a substrate stack may be integrated by fastening the entire substrate stack using fastening members, instead of the adhesive.

Figure 7:
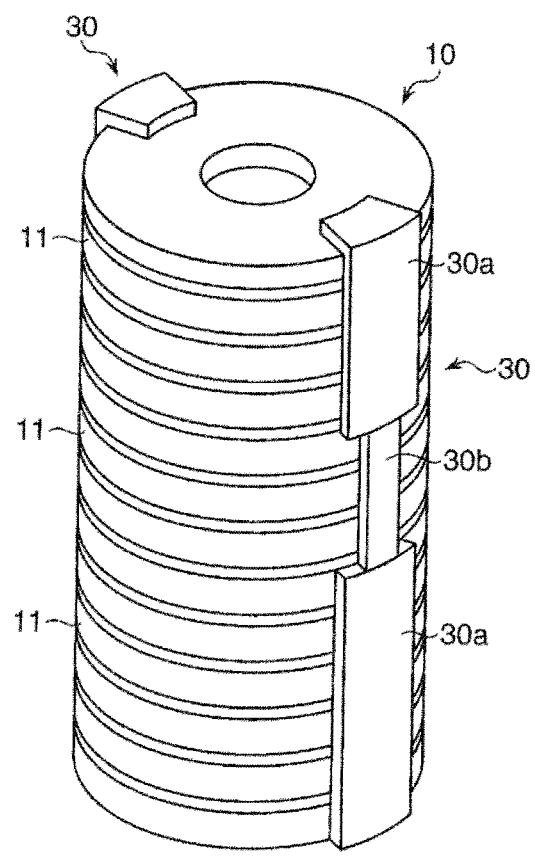
FIG. 7 is a perspective view illustrating a filtration filter clamped by fastening members.

FIG. 7 is a perspective view illustrating a filtration filter clamped by fastening members.

In FIG. 7, the filtration filter 10 is fastened and integrated in the longitudinal direction in FIG. 7 by two oppositely arranged fastening members 30.

Each fastening member 30 include two hook type non-elastic portions 30a which form the opposite ends and an elastic portion 30b interconnecting the two non-elastic portions. The non-elastic portions 30a are formed of a metal, for example, stainless steel, and the elastic portion 30b includes a spring member, of which the main component is stainless steel. By applying these fastening members 30, the respective substrates 11 which are the constituent elements of the filtration filter 10 are restrained within a predetermined extent in movement in the vertical direction in FIG. 7 and the structure as a cylindrical filtration filter may be secured since deviation in the width direction may be suppressed. However, the fastening force of the fastening members 30 is adjusted so that the thermal expansion of the pillars disposed between the substrates 11 may be allowed by the elasticity of the elastic portions 30b. As the material used for the elastic portions 30b, a flexible organic material such as rubber may be used as a consumable product by forming the elastic portions 30b in an easily exchangeable structure, besides the spring member.

In the present exemplary embodiment, as to the flow direction of the liquid to be treated A, it has been described that the liquid to be treated A flows into the cylindrical filtration filter 10 from the outer circumferential surface of the cylindrical filtration filter 10, passes through the flow path 17 formed along the central axis and flows out from the filtration filter 10 as up-flow. However, the flow direction of water in the filtration filter 10 according to the present exemplary embodiment is not limited to this. The flow path 17 formed along the central axis of the cylindrical filtration filter 10 may be used as an entry path and the liquid to be treated A may be adapted to flow in the gaps between the substrates 11 through the entry path and to flow out from the outer circumferential surface.

Figure 8:
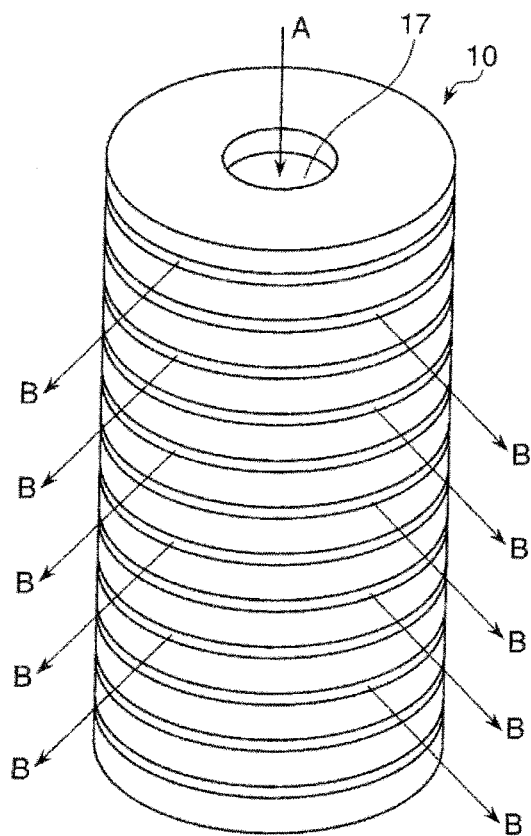
FIG. 8 is an explanatory view illustrating another use situation of the filtration filter.

FIG. 8 is an explanatory view illustrating another use situation of the filtration filter.

Referring to FIG. 8, the liquid to be treated A flows into the filtration filter 10 from the top side, flows through the flow path 17 formed along the central axis of the cylindrical filtration filter 10 as downward flow, flows in respective gaps between the substrates 11, and then, flows out from the filtration filter 10 as a treated liquid B through the openings on the outer circumferential surface. Here, the filtration surface in the filtration filter 10 is formed by the surfaces that interconnect the inner surfaces of the thick wall portions 12 of the respective substrates 11, and the contaminants contained in the liquid to be treated A are trapped by the filtration surface that interconnects the inner surfaces of the thick wall portions 12. When the spacing between the substrates 11 is changed according to a height, the filtration filter 10 may be used as a fractionation apparatus for fine solid materials contained in the liquid to be treated.

In addition, when the liquid to be treated A is caused to flow in the direction as illustrated in FIG. 8, the pressure applied to the filtration filter 10 acts in the direction of widening the spacing between the substrates 11. Thus, when a high pressure filtration is performed, it is desirable to set the flowing direction of the liquid to be treated A to the direction as illustrated in FIG. 1.

In the present exemplary embodiment, although a case in which one through hole 14 is provided at the central portion of each substrate 11 has been described, the through hole 14 may be formed by an aggregate of plural small through holes.

Figure 9:
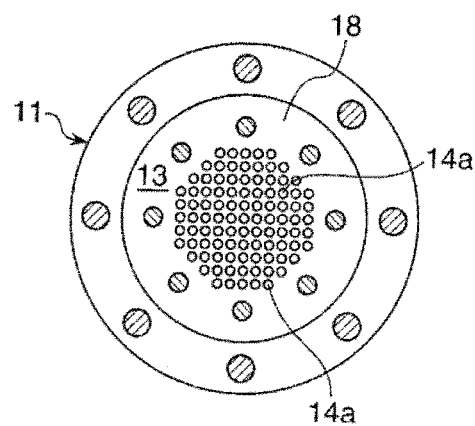
FIG. 9 is a view illustrating a modified example of the substrate of the present exemplary embodiment.

FIG. 9 illustrates a modified example of the substrate 11 of the present exemplary embodiment.

Referring to FIG. 9, a plurality of small through holes 14a are provided at the central portion of the thin wall portion 13 that forms the bottom of the spot face portion 18a of the substrate 11. The aggregate of through hole 14a forms a flow path 17 along the central axis in the filtration filter 10 formed by stacking the substrates 11. In this case, although the manufacturing costs may be increased due to the complicated structure, the strength of the substrates 11 may be increased.

Next, a filtration filter according to a second exemplary embodiment of the present disclosure will be described.

The filtration filter according to the second exemplary embodiment is the same as the filtration filter according to the first exemplary embodiment in basic structure including the fact that, in a substrate stack in which a plurality of substrates having a thick wall portion and a thick wall portion are stacked, the opening width in the filtration surface is defined by the spacing between the thick wall portions of the respective substrates.

The filtration filter according to the second exemplary embodiment is different from the filtration filter according to the first exemplary embodiment in that the length of the thick wall portion of each substrate is set to be longer than the perimeter portion of the substrate so as to secure a wide filtration area.

Figure 10:
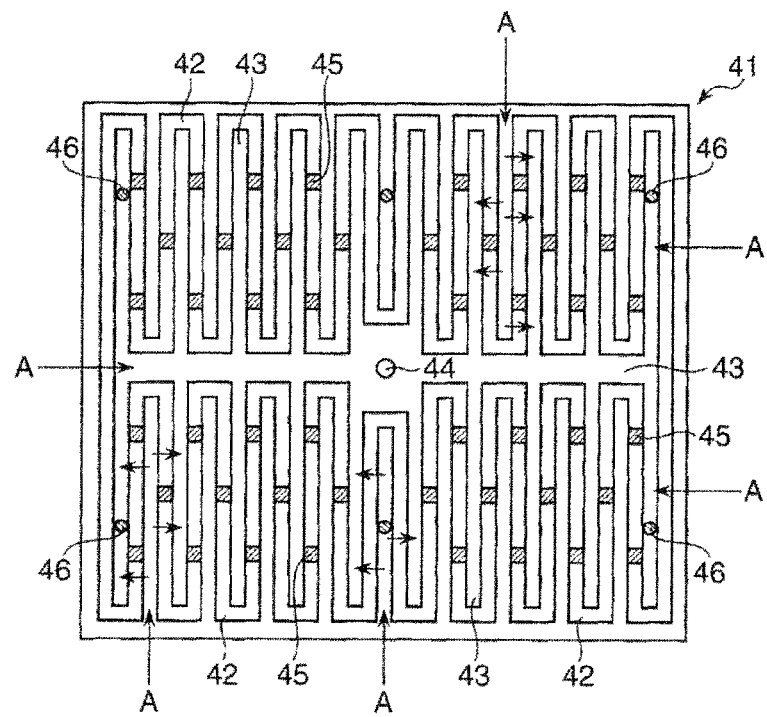
FIG. 10 is a plan view illustrating a substrate applied to a second exemplary embodiment of the present disclosure.
Figure 11:
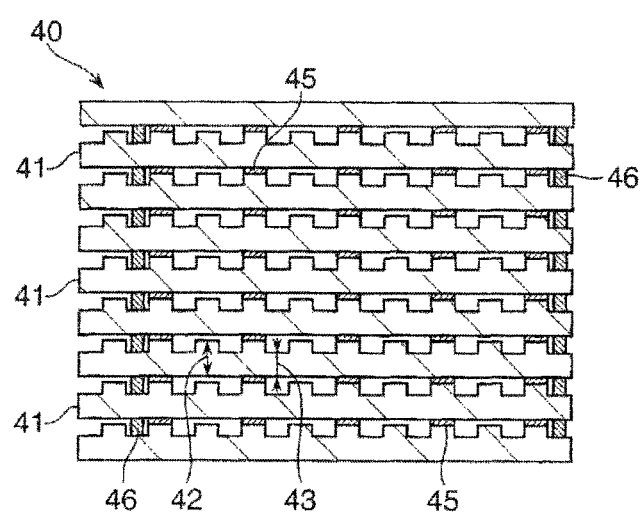
FIG. 11 is a cross-sectional view illustrating a principal portion of the filtration filter formed by stacking a plurality of the substrates of FIG. 10.

FIG. 10 is a pan view of a substrate applied to the second exemplary embodiment of the present invention, and FIG. 11 is a cross-sectional view illustrating a principal portion of the filtration filter formed by stacking a plurality of the substrates as illustrated in FIG. 10.

In FIG. 10, the substrate 41 is a rectangular plate member, and includes thick wall portions 42 and a thin wall portion 43. The thick wall portions 42 are arranged in upper and lower regions of the substrate 41 depicted in FIG. 10 in two rows of zigzag shapes in which folds are repeated, and the thick wall portions 42 in the two rows of zigzag forms are interconnected with each other at respective ends thereof, thereby entirely forming one loop-shaped thick wall portion. The thin wall portion 43 is formed to be surrounded by the loop-shaped thick wall portion 42, and a through hole 44 penetrating the substrate 41 in the thickness direction is provided at the central portion of the substrate 41 in the thin wall portions 4.

On the thick wall portions 42, a plurality of stoppers 45 of a prismatic pillar shape as first spacing maintaining members are provided to be spaced apart from each other. The shape of the stoppers 45 is not limited to the prismatic pillar shape and may be a cylindrical pillar shape or any other pillar shape. In addition, on the thin wall portions 43, a plurality of pillars 46 as second spacing maintaining members are provided to be spaced apart from each other. The shape of the pillars 46 is, for example, a cylindrical pillar shape but is not limited thereto.

Referring to FIG. 11, a plurality of the substrates 41 are stacked via the plurality of stoppers 45 and the plurality of pillars 46, thereby forming a filtration filter 40 of a prismatic pillar shape.

Next, the method of producing the filtration filter according to the present exemplary embodiment will be described.

First, silicon wafers of, for example, a disc shape, are prepared as raw substrates used when producing substrates. The silicon wafers have a smooth surface in which the diameter of each silicon wafer is, for example, 50 mm to 450 mm and the thickness is, for example, 0.1 mm to 3 mm. The surface roughness of the silicon wafers is not more than ⅒ of the gaps between the thick wall portions 42 of the substrates 41 in the filtration filter 40, preferably, for example, 0.1 nm. As the raw substrate, a glass plates, a ceramic plate, or a metal plate may be used, besides the silicon wafer.

Next, a thick wall portion 42 of a zigzag shape is formed on the front surface of each silicon wafer. In forming the thick wall portion 42, a semiconductor manufacturing technology may be suitably used. That is, a silicon wafer is accommodated and supported in, for example, a processing chamber of a plasma etching apparatus, a mask material corresponding to the thick wall portion 42 of the zigzag shape is disposed on the silicon wafer, and then, a plasma etching is performed, thereby forming the thick wall portion 42 of the zigzag shape which remains without being etched and the thin wall portion 43 surrounded by the thick wall portion 42. Here, from one disc-shaped silicon wafer, for example, four substrates arranged in two tiers and two rows are formed on the front surface of the silicon wafer, and then the silicon wafer is cut, thereby producing the substrates 41.

Figure 12:
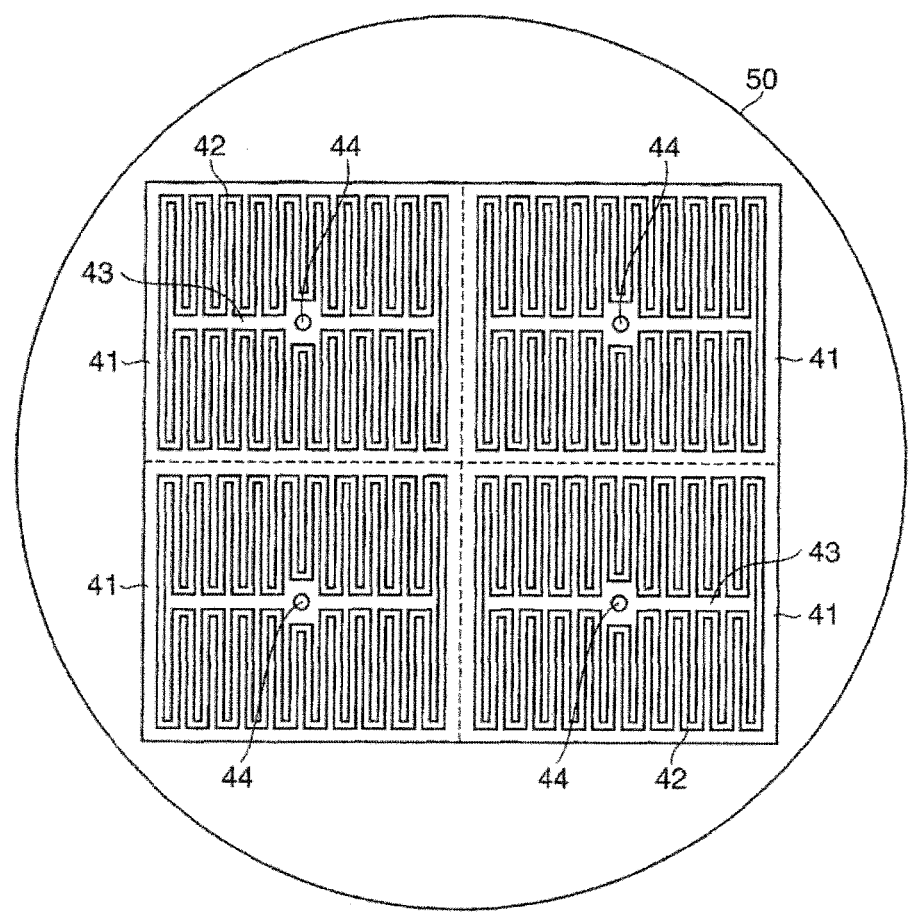
FIG. 12 is a plan view illustrating four substrates formed on a silicon wafer when four substrates are cut from one silicon wafer.

FIG. 12 is a plan view illustrating four substrates 41 formed on a silicon wafer 50 when four substrates 41 are cut from one silicon wafers 50.

Referring to FIG. 12, on the disc-shaped silicon wafer 50, four substrates 41 which have a thick wall portion 42 formed in a zigzag shape and a thin wall portion 43 surrounded by the thick wall portion 42 are formed in two tiers and two rows. The substrates 41 formed in this manner are cut according a known method. Stoppers and pillars are omitted in FIG. 12.

One side of the substrates 41 is, for example, 40 mm to 400 mm, the thickness of each thick wall portion 42 is, for example 0.1 mm to 3 mm, the width of the thick wall portion 42 is, for example, 0.45 mm to 10 mm, and the thickness of each thin wall portion 43 is, for example, 0.1 mm to 3 mm. In addition, the entire length of the thick wall portion 42 in one substrate 41, for example, 1,600 mm to 16,000 mm which is about 10 times of the length of the thick wall portion arranged along the perimeter portion of the substrate 41. The diameter of the through hole 44 is, for example, 10 mm. The through hole 44 is communicated with the through holes 44 of the substrates 41 adjacent thereto in the filtration filter formed by stacking the substrates 41, thereby forming a central flow path through which a liquid to be treated or a filtrate flows.

Next, on the obtained thick wall portion 42 of the obtained substrates 41, stoppers 45 as the first spacing maintaining members that define the spacing between the substrates 41 are formed in the same manner as the first exemplary embodiment (see FIGS. 10 and 11). The stoppers 45 are cylindrical pillar members which are made up of, for example, platinum, polyimide, ceramics, glass, silicon, SiC and formed by, for example, a chemical vapor deposition (CVD) method. In the rectangular cross-section of each stopper 45, the length of one side is defined as, for example, 0.1 mm 10 mm, and the height is defined as, for example, 10 nm to 20 nm according to target materials to be filtered, and the stoppers 45 are formed, for example, at an equidistant interval and by the number required for the spacing between adjacent substrates.

Next, a plurality of pillars 46 as the second spacing maintaining members are disposed at arbitrary places on the thin wall portions 43 of the substrates 41 which have been formed with the stoppers 45 on the thick wall portion 42. The pillars 46 are arranged, for example, at an equidistant interval in the same manner as the first exemplary embodiment. The pillars 46 are separately formed according to a known method. The number and interval of the pillars 46 are not particularly limited, and may be acceptable if the number and interval of the pillars 46 allow the spacing between adjacent substrates 41 to be correctly defined as a predetermined value when the pillars 46 are heated and thermally expanded.

The pillars 46 are made up of a material of which the thermal expansion coefficient is larger than that of the material of the stoppers 45, for example, aluminum, and, when the pillars 46 are arranged on the thin wall portion 43, the top end surfaces of the pillars 46 are adjusted to have a height where the top end surfaces form a coplanar plane with the top end surfaces of the stoppers 45. Besides the aluminum, for example, gold (Au), zinc, silver, chrome, tin, iron, copper, lead, nickel, aluminum, bronze, brass, duralumin, stainless steel may be suitably used as the material of the pillars 46. In addition, besides the metals, for example, a photoresist, polyester, polyethylene, polyvinyl chloride, polystyrene, and polycarbonate may also be used. Since these materials have a relatively large heat expansion coefficient and thus, the expansion length when heated is long, the gaps between the substrates 41 when heated may be widened.

Next, the substrates 41 on which the stoppers 45 and the pillars 46 are arranged are sequentially stacked to form a filtration filter 40 as a substrate stack (see FIG. 11). In this case, an adhesive may be applied to required portions such as the stoppers 45 as needed. An elastic adhesive is applied so as to allow the thermal expansion of the pillars 46.

In the filtration filter 40 formed in this manner, a liquid to be treated A flows into the filtration filter 40 through the gaps between the respective substrates 41 of the filtration filter 40 of the prismatic pillar shape, that is, the gaps between the portions of the thick wall portion 42 arranged in a zigzag shape, flows into the thin wall portion 43 as a filtrate, of which the contaminants have been removed by the filtration surfaces formed by the thick wall portion 42, and then flows toward the central portions of the substrates 41 so that the filtrate flows through the through hole 44 provided at the central portions of the substrates as, for example, up-flow, thereby being recovered.

According to the present exemplary embodiment, the thick wall portion 42 is arranged in a zigzag shape in each substrate 41 so that the length of the thick wall portion 42 is longer than the length of the perimeter portion of the substrate 41. As a result, the filtration may be remarkably increased and as a result, the filtration efficiency of a liquid to be treated may be enhanced.

Also, in the present exemplary embodiment, the length of the pillars 46 is set to be longer than the length of the stoppers 45, and a material of which the thermal expansion coefficient is larger than the constituent material of the stoppers 45 is applied as the constituent material of the pillars 46. Thus, as in the first exemplary embodiment, at normal temperature, the spacing between the substrates 41 may be stably defined by the stoppers 45, and during heating, the pillars 46 are thermally expanded by the heated water so that the spacing between the substrates 41 may be widened. As a result, a stable opening may be obtained during the filtration treatment, and when clogged, the filtration filter may be easily regenerated. The flowing direction of the heated water is typically in reverse to the flowing direction during the filtration treatment but may be the forward direction.

In the present exemplary embodiment, the area of the thin wall portion 43 in each substrate 41 is preferably not more than 30% of the area of the substrate 41. By this, it becomes easy to secure the strength of the substrate. In addition, the diameter of the through hole 44 is preferably, for example, 1 mm to 10 mm, so as to secure the residence time of the liquid to be treated within the filtration filter 40. The through hole 44 may be formed through, for example, a dry etching or a machining.

In the present exemplary embodiment, four substrates 41 formed in two tiers and two rows on the front of the silicon wafer 50 may be cut as one unit and a substrate stack may be formed by stacking a plurality of such substrates 41.

Figure 13:
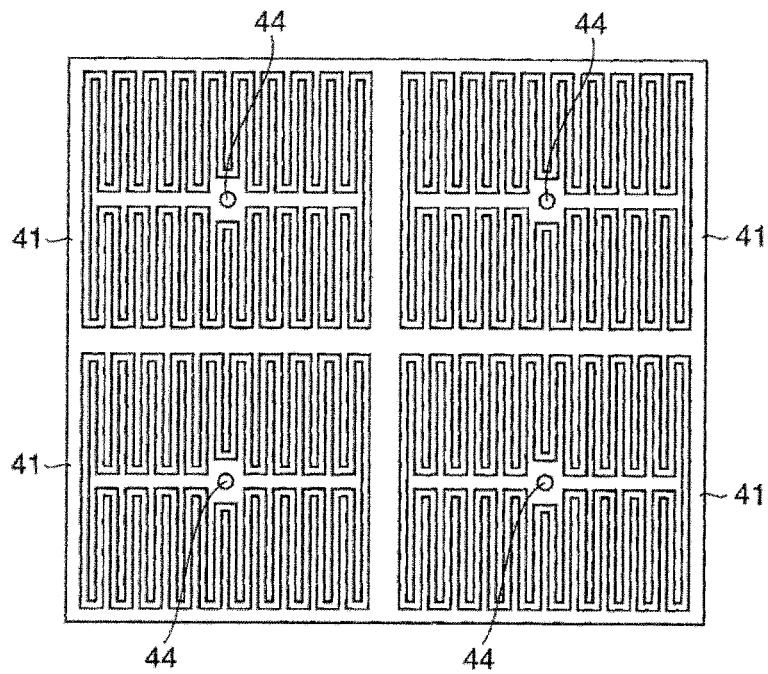
FIG. 13 is a plan view illustrating a substrate aggregate which includes four substrates as one unit.

FIG. 13 is a plan view illustrating a substrate aggregate which takes four substrates 41 as one unit.

In FIG. 13, a substrate aggregate including four substrates cut from the silicon wafer 50 is illustrated. A filtration filter may be formed by stacking a plurality of such substrate aggregates in the same manner as the second exemplary embodiment. In addition, a filtration filter may be formed by stacking a plurality of silicon wafers 50 each of which is formed with such a substrate aggregate, without cutting the substrate aggregates. With this filtration filter, the same effect as that of the second exemplary embodiment may be obtained. In FIG. 13, the stoppers and pillars are also omitted as in FIG. 12.

Although the shape of the thick wall portion 42 on each substrate 41 is formed in a zigzag shape in the present exemplary embodiment, the shape of the thick wall portion 42 is not limited to this and may have, for example, a dual spiral shape configured to surround the thin wall portion 43.

Next, a filtration filter according to a third exemplary embodiment of the present disclosure will be described.

The filtration filter of the present exemplary embodiment is the same as those of the first and second exemplary embodiment in basic structure, including the fact that in a substrate stack formed by stacking a plurality of substrates each having a thick wall portion and a thin wall portion, the spacing between the thick wall portions of the respective substrates defines the opening width in the filtration surface.

Figure 14:
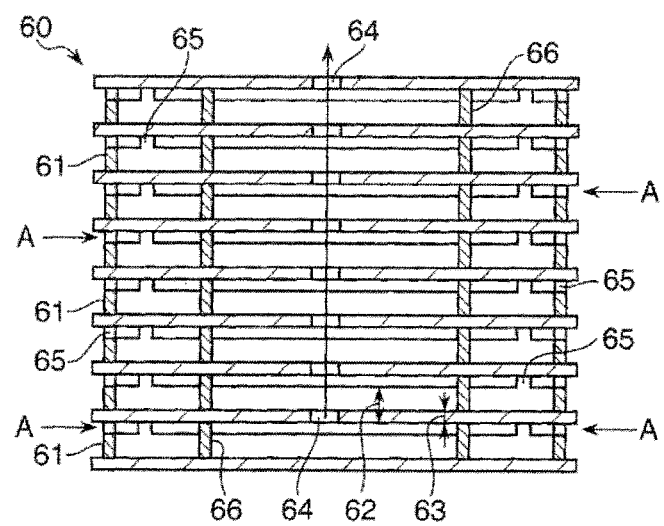
FIG. 14 is a cross-sectional view illustrating a principal portion of a filtration filter according to a third exemplary embodiment of the present disclosure.

FIG. 14 is a cross-sectional view illustrating a principal portion of the filtration filter according to the third exemplary embodiment of the present disclosure. In FIG. 14, the filtration filter 60 is formed by stacking a plurality of substrates 61 having the thick wall portion 62 and the thin wall portion 63. The filtration filter according to the third exemplary embodiment is characterized by the producing method thereof.

Hereinafter, a method of producing the filtration filter 60 will be described.

FIGS. 15A to 15F are process views illustrating the method of producing the filtration filter according to the third exemplary embodiment of the present invention.

Referring to FIGS. 15A to 15F, the filtration filter 60 is produced in the following manner. Each of FIGS. 15A to 15F illustrates a side view and plan view of a substrate in each producing process as a set in which the upper side view is the side view and the lower side view is the plan view.

Figure 15A:
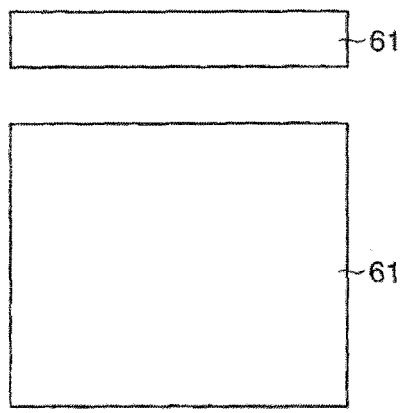
FIG. 15A is a process view illustrating a method of producing the filtration filter according to the third exemplary embodiment of the present disclosure.

When producing the filtration filter 60, a substrate 61 is prepared as a constituent material, first (FIG. 15A). The substrate 61 is, for example, a flat silicon substrate having smooth surfaces on the front and rear side. One side of the substrate 61 is, for example, 5 mm to 450 mm. The thickness is, for example, 0.8 mm to 1.2 mm. The surface roughness of the silicon substrate is not more than ⅒ of the gaps between the thick wall portions 62 when such substrates 61 are stacked, for example, about 0.1 nm.

Figure 15B:
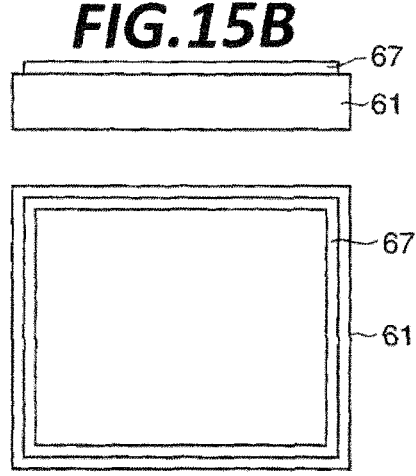
FIG. 15B is a process view illustrating a method of producing the filtration filter according to the third exemplary embodiment of the present disclosure.

Next, a mask material 67 having a line width of, for example, 0.8 mm to 1.2 mm is coated slightly inside of the perimeter portion of the substrate 61, for example, inside by 1 mm to 10 mm from the perimeter portion around the entire circumference along the perimeter portion (FIG. 15B). As for the mask material 67, for example, a super heat resistant and cold resistant polyimide (trademark name: Kapton) or a photoresist used when manufacturing semiconductor devices may be suitably used.

Figure 15C:
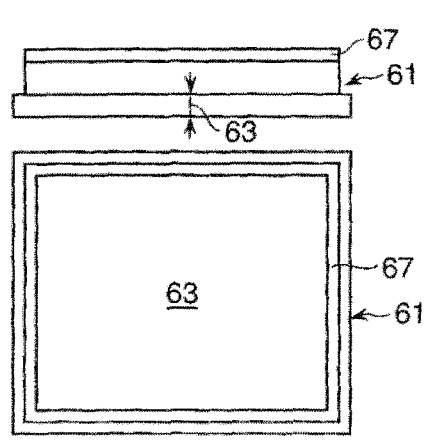
FIG. 15C is a process view illustrating a method of producing the filtration filter according to the third exemplary embodiment of the present disclosure.

Next, the substrate 61 coated with the mask material 67 is accommodated in a chamber of a substrate processing apparatus, the pressure within the chamber is set to, for example, 1 mTorr to 1,000 mTorr (0.133 Pa to 133 Pa), and the substrate 61 is etched in the thickness direction to a depth of, for example, 300 μm using, for example, a mixture gas of HBr, ammonia ($NH_3$) and oxygen ($O_2$) as an etching gas, thereby forming a thin wall portion 63 surrounded by a convex portion covered by the mask material 67 (FIG. 15C).

Figure 15D:
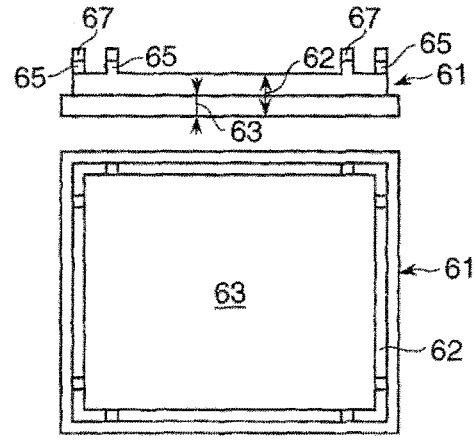
FIG. 15D is a process view illustrating a method of producing the filtration filter according to the third exemplary embodiment of the present disclosure.
Figure 15E:
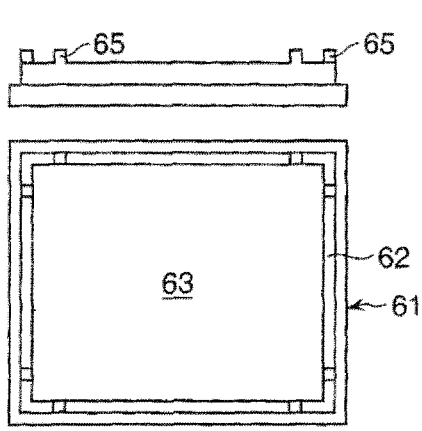
FIG. 15E is a process view illustrating a method of producing the filtration filter according to the third exemplary embodiment of the present disclosure.

Subsequently, a portion of the mask material 67, that is, a portion other than the portion which will form the stoppers 65 as the spacing maintaining units, is peeled off and a plasma etching processing is performed with the above-mentioned conditions, thereby forming the thick wall portion 62 and the stoppers 65 that protrude from the thick wall portion 62 (FIG. 15D). Here, the height of the stoppers 65 is adjusted to a height that corresponds to a size of target components to be removed with the filtration filter 60, for example, 1 nm to 100,000 nm. The number and interval of the stoppers 65 are not particularly defined and may be acceptable if they allow the spacing between the substrates 61 to be maintained stably.

Figure 15F:
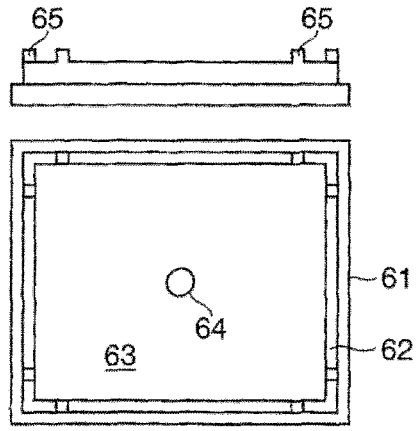
FIG. 15F is a process view illustrating a method of producing the filtration filter according to the third exemplary embodiment of the present disclosure.

Next, the mask material 67 is peeled off from the stoppers 65 of the substrate 61 formed with the stoppers 65 (FIG. 15E), and a through hole 64 is formed at the central portion of the thin wall portion 63, thereby completing the substrate 61 as a constituent element of the filtration filter 60 (FIG. 15F).

Next, a plurality of pillars 66 as spacing maintaining members are arranged at an equidistant interval at arbitrary positions on the thin wall portion 63 of the obtained substrate 61 as in the first and second exemplary embodiments, and a plurality of such substrates 61 (e.g., dozens of substrates to 100 substrates) are stacked via the pillars 66 and the stoppers 65, thereby forming the filtration filter 60.

According to the present exemplary embodiment, the formation of the thick wall portion 62 and the thin wall portion 63 and the subsequent formation of the stoppers 65 may be executed by the plasma etching processing. Thus, the producing process may be simplified and thus, productivity may be improved.

Also in the present exemplary embodiment, a material of which the thermal expansion coefficient is larger than the constituent material of the stoppers 65, i.e., the material of the substrates 61, is applied as the constituent material of the pillars 66, as in the first and second exemplary embodiments. In addition, when the height of the pillars 66 is set to be higher than the stoppers 65, specifically, to be equal to or slightly longer than the sum of the difference between the thick wall portion 62 and the thin wall portion 63 and the height of the stoppers 65, at normal temperature, the spacing between the substrates 61 may be stably defined by the stoppers 65 and at the time of regeneration where heated water is caused to flow therethrough, the pillars 66 are thermally expanded so that the spacing between the substrates 61 may be widened. Thus, stable openings may be obtained during a filtration treatment and when clogged, the filtration filter may be easily regenerated and repeatedly used.

In the present exemplary embodiment, for example, liquid to be treated A flows into the body of the filtration filter 60 from the gaps between the substrates 61 on the outer circumferential surface of the filtration filter 60 (see FIG. 14) and becomes filtrate of which the target components are filtered by the gaps between the thick wall portions 62. The filtrate flows through the central flow path in which the through holes 64 formed at the central portions of the substrates 61 (see FIG. 15F) are communicated with each other) as, for example, up-flow, and flows out from the filtration filter 60. In addition, the liquid to be treated A may be caused to flow into the filtration filter 60 as, for example, downward flow, and then to flow toward the outer circumferential surface of the filtration filter 60 through the gaps between the respective substrates 61.

In the present exemplary embodiment, the shape of the substrates 61 is a rectangular plate shape. However, the shape of the substrates 61 is not particularly limited and may be a disc shape, an oval plate shape or any other plate shape, and the substrates 61 may be applied when forming the filter according to the first or second exemplary embodiment.

In the present exemplary embodiment, a super heat resistant and cold resistant polyimide (trademark name: Kapton) or photoresist as the mask material. However, besides these materials, for example, a metal, carbon or quartz, may be used. In addition, in the present exemplary, the filtration filter 60 may be integrated using, for example, elastic fastening members as illustrated in FIG. 7 or an elastic adhesive. By this, the shape as the filtration filter 60 may be stabilized.

In the present exemplary embodiment, as for the constituent material of the pillars 66, a material which has a converse piezoelectric effect such as, for example, crystal ($SiO_2$), zinc oxide (ZnO), Rochelle salt (potassium sodium tartrate) ($KNaC_4H_4O_6$), lead zirconate titante ($PZT:Pb(Zr,Ti)O_3$), gemstone (tourmaline), polyvinylidene fluoride (PVDF), gallium phosphate ($GaPO_4$), or gallium arsenide (GaAs), may be used, instead the material of which the thermal expansion coefficient is higher than that of the constituent material of the stoppers 65.

Although the exemplary embodiments of the present disclosure have been described in detail above, the present disclosure is not limited to these exemplary embodiments.

DESCRIPTION OF SYMBOL

10, 60: filtration filter
11, 41, 61: substrate
12, 42, 62: thick wall portion
13, 43, 63: thin wall portion
14, 14a, 44, 64: through hole
15, 45, 65: stopper
16, 46, 66: pillar
17: flow path
18: spot face portion
67: mask material

What is claimed is:

1. A filtration filter comprising:
 a substrate stack formed by stacking a plurality of substrates each having a through hole that penetrates a substrate from front to back;
 one or more first spacing maintaining members that define a spacing between adjacent substrates in the substrate stack; and
 one or more second spacing maintaining members having a thermal expansion coefficient that is larger than that of the one or more first spacing maintaining members,
 wherein the spacing between adjacent substrates at normal temperature is defined at least by the one or more first spacing maintaining members, the spacing when heated is defined by the one or more second spacing maintaining members in a thermally expanded state, and gaps between adjacent substrates form a filtration surface that traps target components contained in a liquid to be treated.

2. The filtration filter of claim 1, wherein the substrates have a thick wall portion and a thin wall portion, wherein the one or more first spacing maintaining members includes a plurality of first spacing maintaining members, and the plurality of first spacing maintaining members are disposed between the thick wall portions to be spaced apart from each other, wherein the one or more second spacing maintaining members includes a plurality of second spacing maintaining members, and the plurality of second spacing maintaining members are disposed between the thin wall portions to be spaced apart from each other, and a length of each of the plurality of second spacing maintaining members is longer than a length of each of the plurality of first spacing maintaining members.

3. The filtration filter of claim 2, wherein the thick wall portion forms a perimeter portion of each substrate, the thin wall portion includes a central portion of the substrate which is surrounded by the thick wall portion, and the through hole is provided through the central portion of the thin wall portion.

4. The filtration filter of claim 2, wherein the thick wall portion is provided on the front of each substrate, and wherein the thick wall portion has a length which is longer than a length of a perimeter portion of the substrate, the thin wall portion is surrounded by the thick wall portion, and the thin wall portion includes a central portion of the substrate, and the through hole is provided through the central portion of the substrate.

5. The filtration filter of claim 2, wherein the thick wall portion is arranged on the front of each substrate in a loop shape in which two rows of zigzag-shaped line portions are connected to each other at ends thereof, respectively.

6. The filtration filter of claim 1, wherein the through hole of each substrate communicates with through holes of other substrates in the substrate stack, thereby forming a flow path for the liquid to be treated or a filtrate.

7. The filtration filter of claim 2, wherein the thick wall portion of the substrate has a surface roughness (Ra) which is not more than $\frac{1}{10}$ of a gap between the thick wall portions.

8. The filtration filter of claim 1, wherein each of the plurality of substrates is made up of at least one of silicon, glass, a metal, a silicon compound including silicon carbonate, a resin including polyimide, and carbon.

9. The filtration filter of claim 1, wherein the substrate stack is integrated by a fastening member which allows the thermal expansion of the second spacing maintaining members.

10. A method of producing a filtration filter, the method comprising:
 forming a spot face portion at a central portion of a substrate, thereby forming a thick wall portion that forms a perimeter portion of the substrate and a thin wall portion surrounded by the thick wall portion;

forming a through hole that penetrates the substrate from front to back at a central portion of the thin wall portion;

forming a plurality of first spacing maintaining members with a predetermined height at a predetermined interval on the thick wall portion;

forming a plurality of second spacing maintaining members on the thin wall portion at a predetermined interval, each of the second spacing maintaining members having a thermal expansion coefficient larger than that of the first interval maintaining members and being longer than the first spacing maintaining members; and stacking a plurality of substrates via at least the first interval maintaining members.

11. The method of claim 10, wherein, in the forming a spot face portion step, the spot face portion is formed through a plasma etching using plasma.

12. The method of claim 10, wherein, in the forming a spot face portion step, the spot face portion is formed through a chemical mechanical polishing (CMP) method.

13. The method of claim 10, wherein, in the forming a plurality of first spacing maintaining members step, the first spacing maintaining members are formed on the thick wall portion through a film forming method using a mask material.

14. The method of claim 10, wherein, in the forming a plurality of first spacing maintaining members step, the first spacing maintaining members made up of a photoresist are formed on the thick wall portion through a coating method using a mask material.

15. The method of claim 10, further comprising:
integrating the substrate stack stacked in the stacking step by a fastening member which allows thermal expansion of the second spacing maintaining members.

16. The method of claim 10, wherein the thick wall portions of the substrates have a surface roughness (Ra) which is not more than 1/10 of the gaps between the thick wall portions.

17. The method of claim 10, wherein at least one of a silicon plate, a glass plate, a metal plate, a plate of a silicon compound including silicon carbonate, a plate of a resin including polyimide, and a carbon plate is used as the substrates.

18. A method of producing a filtration filter, comprising:
forming an annular masking material along a perimeter portion of a front surface of a substrate;

etching the substrate formed with the annular masking material so that a thin wall portion surrounded by a convex portion which corresponds to the annular masking material is formed;

peeling a part of the masking material on the convex portion after the etching step of the substrate formed with the annular masking material is terminated;

etching the substrate after the peeling step of the part of the masking material on the convex portion so that a thick wall portion is formed by the convex portion other than a portion coated with the masking material remaining after the peeling step and a spacing maintaining portion protruding from the thick wall portion is formed by the convex portion of the portion coated with the remaining masking material;

forming a through hole that penetrates the substrate from front to back at a central portion of the thin wall portion surrounded by the thick wall portion;

forming a plurality of spacing maintaining members on the thin wall portion of the substrate formed with the through hole at a predetermined spacing, each of the plurality of spacing maintaining members having a thermal expansion coefficient larger than that of the spacing maintaining portion and having a height higher than that of the spacing maintaining portion;

peeling the masking material from the spacing maintaining portion; and stacking a plurality of substrates at least via the spacing maintaining portion.

19. The method of claim 18, further comprising integrating the substrate stack stacked in the stacking step by a fastening member that allows thermal expansion of the spacing maintaining member.

20. The method of claim 18, wherein the surface roughness (Ra) of the thick wall portions of the substrates is not more than 1/10 of the gaps between the thick wall portions.

21. The method of claim 18, wherein at least one of a silicon plate, a glass plate, a metal plate, a plate of a silicon compound including silicon carbonate, a plate of a resin including polyimide, and a carbon plate is used as the substrates.

* * * * *